United States Patent [19]

Wovcha et al.

[11] 4,175,006

[45] Nov. 20, 1979

[54] COMPOSITION OF MATTER AND PROCESS

[75] Inventors: Merle G. Wovcha; Frederick J. Antosz, both of Kalamazoo; John M. Beaton, Portage; Alfred B. Garcia, Kalamazoo; Leo A. Kominek, Portage, all of Mich.

[73] Assignee: The Upjohn Company, Kalamazoo, Mich.

[21] Appl. No.: 844,366

[22] Filed: Oct. 21, 1977

[51] Int. Cl.² ............................................. C07B 29/02
[52] U.S. Cl. ..................................... 435/55; 435/865; 435/52
[58] Field of Search ............................ 195/51 G, 51 S

[56] References Cited

U.S. PATENT DOCUMENTS

| | | | |
|---|---|---|---|
| 3,759,791 | 9/1973 | Marsheck et al. | 195/51 G |
| 4,057,469 | 11/1977 | Nishikawa et al. | 195/51 G |

*Primary Examiner*—Alvin E. Tanenholtz
*Attorney, Agent, or Firm*—Roman Saliwanchik

[57] ABSTRACT

Valuable steroid intermediates, 9α-hydroxyandrost-4-ene-17β-ol-3-one (9α—OH testosterone), 9α-hydroxy-3-ketobisnorchol-4-en-22-ol (9α—OH BN alcohol) and 9α—hydroxy-3-ketobisnorchol-4-en-22-oic methyl ester (9α—OH BN acid methyl ester), prepared by microbiological conversion of steroids having 17-alkyl side chains of 8 to 10 carbons.

11 Claims, No Drawings

COMPOSITION OF MATTER AND PROCESS

BACKGROUND OF THE INVENTION

U.S. Pat. No. 4,029,549 discloses and claims a steroid conversion process for making 9α-hydroxy-3-ketobisnorchol-4-en-22-oic acid (9α-OH BN acid). The process can be conducted using a mutant of a variety of steroid degrading microorganisms. The mutation process to prepare the mutants is disclosed in the patent. Specifically exemplified is the use of *Mycobacterium fortuitum* NRRL B-8119.

U.S. Pat. No. 4,035,236 discloses and claims a process for preparing 9α-hydroxyandrostenedione (9α-OH AD). This compound is also produced by the process as disclosed in U.S. Pat. No. 4,029,549.

The presence of additional compounds in the fermentation beers disclosed in the above patents was previously recognized, but the identity of the compounds was not known prior to the date of the subject invention. These additional compounds were subsequently shown by advanced identification techniques to be useful steroid intermediates as disclosed herein. Of these compounds, 9α-OH testosterone is a known compound, whereas the others are novel.

BRIEF SUMMARY OF THE INVENTION

9α-OH testosterone, 9α-OH BN alcohol and 9α-OH BN acid methyl ester are produced in a fermentation process using the microorganism *Mycobacterium fortuitum* NRRL B-8119. This organism is disclosed and characterized in U.S. Pat. No. 4,029,549. In addition to the characteristics given in said patent, this microorganism is further characterized by its ability to accumulate the compounds disclosed herein under fermentation conditions, also as disclosed herein. Other mutants of Mycobacterium, as well as mutants from the genera of microorganisms disclosed in U.S. Pat. No. 4,029,549, can be used in the subject invention. Examples of suitable steroid substrates are sitosterol, cholesterol, stigmasterol, campesterol, and like steroids with 17-alkyl side chains of from 8 to 10 carbon atoms, inclusive. These steroid substrates can be in either the pure or crude form.

DETAILED DESCRIPTION OF THE INVENTION

The microorganisms which can be used to produce the compounds of the subject invention are the same as disclosed in U.S. Pat. No. 4,029,549. The microorganism specifically exemplified is *Mycobacterium fortuitum*, NRRL B-8119. A subculture of this microorganism is freely available from the depository at the Northern Regional Research Laboratory, U.S. Department of Agriculture, Peoria, Ill., U.S.A., by request made thereto. It should be understood that the availability of the culture does not constitute a license to practice the subject invention in derogation of patent rights granted with the subject instrument by governmental action.

The transformation process of the subject invention is also as disclosed in U.S. Pat. No. 4,029,549.

Also, the procedure for the preparation of *Mycobacterium fortuitum* NRRL B-8119 is as disclosed in U.S. Pat. No. 4,029,549. This process can also be used to prepare mutants of other genera of microorganisms as disclosed in U.S. Pat. No. 4,029,549 and herein.

The isolation of the products of the subject invention from the fermentation broth is accomplished by first removing the major products of the sterol conversions, i.e., 9α-OH AD and 9α-OH BN acid. These major products are recovered from the fermentation beer by first extracting the fermentation beer with a water-immiscible organic solvent for steroids. Suitable solvents are methylene chloride (preferred), chloroform, carbon tetrachloride, ethylene chloride, trichloroethylene, ether, amyl acetate, benzene and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

The extract from the fermentation beer is dried. The resulting solids are taken up in chloroform and sufficient methanol is added to precipitate residual sterols which are then filtered off. The filtrate is dried and the residue dissolved in hot acetone. Upon cooling and subsequent addition of cyclohexane most of the 9α-OH AD is precipitated and recovered by filtration. The filtrate is then dried and the residue dissolved in chloroform and extracted with a saturated sodium bicarbonate solution to remove 9α-OH BN acid. The individual components remaining in the chloroform after the bicarbonate extraction are separated by chromatography on a silica gel column, eluting with chloroform-methanol (98:2).

The first compound to elute is the methyl ester of 9α-OH BN acid. The second compound to elute is residual 9α-OH AD which remains soluble in the acetone-cyclohexane solution described above. The third compound is 9α-OH BN alcohol. The next compound to elute from the column is 9α-OH testosterone.

The compounds of the subject invention are valuable as intermediates in the manufacture of steroids. For example, 9α-OH BN acid methyl ester can be converted to 9(11)-dehydro BN acid by treatment with N-bromoacetamide and sulfur dioxide in pyridine, as disclosed in British Pat. No. 869,815, followed by hydrolysis to generate the 22-carboxyl. 9(11)-Dehydro BN acid can be converted to 9(11)-dehydroprogesterone by, for example, the method described in Ber. 88: 883 (1955), and subsequently to 11β-hydroxyprogesterone as described in JACS 88: 3016 (1966). Treatment of 11β-hydroxyprogesterone with chromic acid yields 11-ketoprogesterone which is a known intermediate in the synthesis of cortisol acetate, a major and highly active cortical steroid [see, for example, Fieser and Fieser, Steroids, page 676, Reinhold (1959)].

9α-OH BN alcohol can be readily converted to 9α-OH BN acid by chromic acid oxidation, then to 9α-OH BN acid methyl ester by treatment with diazomethane and subsequently to 11-ketoprogesterone as described above.

9α-Hydroxy-11-unsubstituted steroids of the androstane series can also easily be dehydrated to the valuable 9(11)-dehydro steroids in accordance with methods known in the art, e.g., with thionyl chloride in the presence of pyridine. The 9(11)-dehydro compounds thus obtained are known intermediates in the production of highly active compounds. For example, the 9(11)-dehydro steroids can be converted to the corresponding 9α-halo-11β-hydroxy compounds in accordance with procedures known in the art, e.g., U.S. Pat. No. 2,852,511 for the preparation of 9α-halo-hydrocortisone. Also, 9α-hydroxy compounds of the androstane series are useful as antiandrogenic, antiestrogenic and antifertility agents.

The following examples are illustrative of the process and products of the subject invention but are not to be construed as limiting. All percentages are by weight and all solvent mixture proportions are by volume unless otherwise noted.

EXAMPLE 1—Preparation of Mutant *M. fortuitum* NRRL B-8119 From *M. fortuitum* ATCC 6842.

(a) Nitrosoguanidine Mutagenesis

Cells of *M. fortuitum* ATCC 6842 are grown at 28° C. in the following sterile seed medium:

| | |
|---|---|
| Nutrient Broth (Difco) | 8 g/liter |
| Yeast Extract | 1 g/liter |
| Sodium Propionate | 0.5 g/liter |
| Distilled Water, q.s. | 1 liter |

The pH is adjusted to 7.0 with 1 N NaOH prior to sterilization at 121° C. for 20 minutes.

The cells are grown to a density of about $5 \times 10^8$ per ml, pelleted by centrifugation, and then washed with an equal volume of sterile 0.1 M sodium citrate, pH 5.6. Washed cells are resuspended in the same volume of citrate buffer, a sample removed for titering (cell count), and nitrosoguanidine added to a final concentration of 50 μg/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile minimal salts medium, minus a carbon source, consisting of the following:

| | |
|---|---|
| $NH_4NO_3$ | 1.0 g/liter |
| $K_2HPO_4$ | 0.25 g/liter |
| $MgSO_4.7H_2O$ | 0.25 g/liter |
| NaCl | 0.005 g/liter |
| $FeSO_4.7H_2O$ | 0.001 g/liter |
| Distilled Water, q.s. | 1 liter |

The pH is adjusted to 7.0 with 1 N HCl prior to sterilization at 121° C. for 20 minutes. The cells are then plated out to select for mutants.

(b) Selection And Isolation Of Mutant *M. fortuitum* NRRL B-8119

Mutagenized cells, as described above, are diluted and spread onto plates containing a medium consisting of the following (modified from Fraser and Jerrel. 1963. J. Biol. Chem. 205: 291-295):

| | |
|---|---|
| Glycerol | 10.0 g/liter |
| $K_2HPO_4$ | 0.5 g/liter |
| $NH_4Cl$ | 1.5 g/liter |
| $MgSO_4.7H_2O$ | 0.5 g/liter |
| $FeCl_3.6H_2O$ | 0.05 g/liter |
| Distilled Water, q.s. | 1 liter |

Agar (15 g/liter) is added, and the medium is autoclaved at 121° C. for 30 minutes and then poured into sterile Petri plates.

Growth on this medium eliminates most nutritional auxotrophes produced by the mutagensis procedure, e.g. cultures that require vitamins, growth factors, etc. in order to grow on chemically defined medium are eliminated. After incubation at 28° C. for about 7 days, the resulting colonies are replicated to test plates suitable for selecting mutants and then back onto control plates containing the glycerol-based medium. The test plates are prepared as described by Peterson, G. E., H. L. Lewis and J. R. David. 1962. "Preparation of uniform dispersions of cholesterol and other water-insoluble carbon sources in agar media." J. Lipid Research 3: 275-276. The minimal salts medium in these plates is as described above in section (a) of Example 1. Agar (15 g/liter), and an appropriate carbon source (1.0 g/liter), such as sitosterol or androstenedione (AD), are added and the resulting suspension autoclaved for 30 minutes at 121° C. The sterile, hot mixture is then poured into a sterile blender vessel, blended for several minutes, and then poured into sterile Petri plates. Foaming tends to be a problem in this procedure but can be reduced by blending when the mixture is hot and by flaming the surface of the molten agar plates. In this manner uniform dispersions of water-insoluble carbon sources are obtained which facilitates the preparation of very homogenous but opaque agar plates.

Colonies which grew on the control plates, but not on test plates containing AD as the sole carbon source, are purified by streaking onto nutrient agar plates. After growth at 28° C., individual clones are picked from the nutrient agar plates with sterile toothpicks and retested by inoculating gridded plates containing AD as the carbon source. Purified isolates which exhibit a phenotype different from the parental culture are then evaluated in shake flasks.

(c) Shake Flask Evaluation

Shake flasks (500 ml) contain 100 ml of biotransformation medium consisting of the following ingredients:

| | |
|---|---|
| Glycerol | 10.0 g/liter |
| $K_2HPO_4$ | 0.5 g/liter |
| $NH_4Cl$ | 1.5 g/liter |
| $MgSO_4.7H_2O$ | 0.5 g/liter |
| $FeCl_3.6H_2O$ | 0.05 g/liter |
| Distilled Water, q.s. | 1 liter |

Soyflour (1 g/liter) is blended into the medium and then sitosterol (10 g/liter) is also blended into the medium. After the flasks are autoclaved for 30 minutes at 121° C., they are cooled to 28° C. and then inoculated with 10 ml of seed growth prepared as follows:

The purified isolates from part (b) are grown on agar slants at 28° C. A loop of cells taken from a slant is used to inoculate at 500-ml flask containing 100 ml of sterile seed medium consisting of the following ingredients:

| | |
|---|---|
| Nutrient Broth (Difco) | 8 g/liter |
| Yeast Extract | 1 g/liter |
| Glycerol | 5 g/liter |
| Distilled Water, q.s. | 1 liter |

The pH is adjusted to 7.0 with 1 N NaOH prior to autoclaving the flasks at 121° C. for 20 minutes. The seed flasks are incubated at 28° C. for 72 hours.

As disclosed above, 10 ml of seed growth is then used to inoculate each 500-ml flask containing 100 ml of sterile transformation medium. The flasks are then incubated at 28° C. to 30° on a rotary shaker and sampled at various intervals. Ten ml samples are removed and extracted by shaking with 3 volumes of methylene chloride. Portions of the extracts are analyzed by thin layer chromatography (tlc) using silica gel and the solvent system described above, i.e., 2:3 (by volume) ethyl acetate-cyclohexane, and by gas-liquid chromatography. Evidence of the presence of 9α-OH AD confirms the selective degradation of sitosterol by the novel mutant produced from the parent *M. fortuitum* ATCC 6842.

EXAMPLE 2

To a medium consisting of 1.0 part of glycerol, 0.15 part of ammonium chloride, 0.05 part of magnesium sulfate heptahydrate, 0.05 part of dipotassium hydrogen phosphate, 0.005 part of ferric chloride hexahydrate, and 100 parts of distilled water is added 0.1 part of soyflour and 1.0 part of sitosterols, N.F. The resultant mixture is sterilized by heating 30 minutes at 121° C., whereupon it is cooled to 30° C. and then inoculated with 10 parts of a seed culture of the mutant *Mycobacterium fortuitum* NRRL B-8119, prepared as described in Example 1(c). The inoculated mixture is incubated at 30° C. for 336 hours with agitation to promote submerged growth. Following incubation, the mixture is extracted with methylene chloride. The extract is filtered through diatomaceous earth and the filtrate is vacuum distilled to dryness. The residue is taken up in 10% chloroform in methanol and then concentrated with nitrogen on a steam bath until crystals appear. The solution is then cooled to room temperature and filtered to remove the precipitated sitosterols. From the supernatant, on evaporation of solvent, good yields of 9α-OH testosterone, 9α-OH BN alcohol and 9α-OH BN acid methyl ester, as well as 9α-OH AD and 9α-OH BN acid are obtained.

EXAMPLE 3

By substituting cholesterol for sitosterol in Example 2 there are obtained the compounds produced in Example 2.

EXAMPLE 4

By substituting stigmasterol for sitosterol in Example 2 there are obtained the compounds produced in Example 2.

EXAMPLE 5

By substituting campesterol for sitosterol in Example 2 there are obtained the compounds produced in Example 2.

EXAMPLE 6

By adding a combination of any of the steroids in Examples 2-5, in addition to sitosterol, or in place of sitosterol, in Example 2 there are obtained the compounds produced in Example 2.

EXAMPLE 7

The products produced in Example 2 can be isolated as separate entities in the essentially pure form by the following procedure. The supernatant of Example 2, containing the products produced in the fermentation, is dried and the residue dissolved in hot acetone. Upon cooling and subsequent addition of cyclohexane most of the major product, 9α-OH AD, is precipitated and recovered by filtration. The filtrate is then dried and the residue dissolved in chloroform and extracted with a saturated sodium bicarbonate solution to remove 9α-OH BN acid. The individual components remaining in the chloroform after the bicarbonate extraction are separated by chromatography on a silica gel column, eluting with chloroform-methanol (98:2 v/v). Fractions containing the same component as determined by tlc are combined and further purified by liquid chromatography or preparative tlc followed by recrystallization, to give more 9α-OH AD plus the compounds of the subject invention.

The mass spectrum of the first eluted compound in its essentially pure form has a molecular ion at 374, and also exhibits intense ions at m/e 124, 136 and 137 confirming its close relationship to 9α-OH AD. The ir spectrum exhibits bands at 3540 and 3400 cm$^{-1}$ (hydroxyl) and also at 1735 cm$^{-1}$ and 1655 cm$^{-1}$ suggesting the presence of two carbonyl groups. Comparison of the $^1$H-nmr spectrum with that of 9α-OH BN acid shows that they are virtually identical except for an additional 3 proton peak at δ3.63 where a methyl ester would be expected. This compound is therefore identified as the methyl ester of 9α-OH BN acid, and confirmation of this is obtained from the $^{13}$C-nmr spectrum which shows signals for 23 carbon atoms including four methyl groups (δ11.1, 17.0 19.8 and 5.13), two carbonyls (δ176.9 and 199.0), two olefinic carbons (δ126.7 and 168.6) and a quaternary carbon atom bearing oxygen (δ76.2).

The second eluted compound in its essentially pure form is residual 9α-OH AD which remains soluble in the acetone-cyclohexane solution described above.

The third component in its essentially pure form has a molecular weight of 346, the mass spectrum of which again exhibits the characteristic ions at m/e 124, 136 and 137. The presence of a hydroxyl group and an unsaturated carbonyl are deduced from infrared peaks at 3400 cm$^{-1}$ and 1650 cm$^{-1}$ and its evident from the doublet centered at δ1.05 in the $^1$H-nmr spectrum that a side chain similar to that of 9α-OH BN acid and 9α-OH BN acid methyl ester is present at C-17. The $^1$H-nmr spectrum in dimethyl sulfoxide-d$_6$ also indicates the presence of both a primary (δ4.18, t, J=5) and a tertiary (δ3.95) alcohol. Signals due to 22 carbon atoms are seen in the $^{13}$C-nmr spectrum, including three methyl groups (δ11.1, 16.7 and 19.9), two olefinic carbons (δ126.6 and 169.4), one carbonyl (δ199.2) and two carbon atoms bearing hydroxyls (δ67.7, triplet and 76.3, singlet). On the basis of the above spectral evidence the structure 9α-hydroxy-3-oxo-23,24-bisnorchol-4-en-22-ol (9α-OH BN alcohol) is assigned to this compound.

The mass spectrum of the next major eluted compound in its essentially pure form from this column shows a molecular ion at 304, and the usual intense ions at 124, 136 and 137. Given the evident close relationship to 9α-OH AD, and the fact that the $^{13}$C-nmr spectrum showed 19 carbon atoms, only one of which was part of a carbonyl group (δ199.3), this compound is identified as 9α-OH testosterone, and the structural assignment is confirmed by comparison with an authentic sample.

EXAMPLE 8

By substituting a microorganism from the genera Arthrobacter, Bacillus, Brevibacterium, Corynebacterium, Microbacterium, Nocardia, Protaminobacter, Serratia, and Streptomyces, in Example 1 for *Mycobacterium fortuitum* ATCC 6842 there are obtained mutant microorganisms which are characterized by their ability to selectively degrade steroids having 17-alkyl side chains of from 8 to 10 carbon atoms, inclusive, and accumulate the products disclosed herein in the fermentation beer.

EXAMPLE 9

By substituting the mutants obtained in Example 8 for *M. fortuitum* NRRL B-8119 in Examples 2-7, there are obtained the products as disclosed herein.

EXAMPLE 10

By substituting a microorganism selected from the group consisting of *Mycobacterium phlei, M. smegmatis, M. rhodochrous, M. mucosum,* and *M. butyricum* for *M. fortuitum* ATCC 6842 in Example 1 there are obtained mutant microorganisms which are characterized by their ability to selectively degrade steroids having 17-alkyl side chains of from 8 to 10 carbon atoms, inclusive, and accumulate the products disclosed herein in the fermentation beer.

EXAMPLE 11

By substituting the mutants obtained in Example 10 for *M. fortuitum* NRRL B-8119 in Examples 2–7, there are obtained the products as disclosed herein.

The structural formulae for the novel compounds of the invention can be shown as follows:

9α-OH BN alcohol

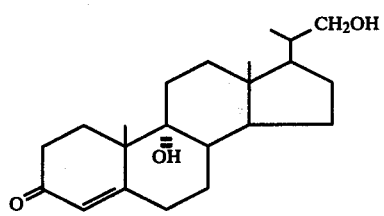

9α-OH BN acid methyl ester

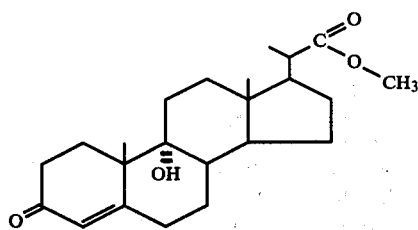

We claim:

1. A process for preparing 9α-OH testosterone in its essentially pure form which comprises cultivating *Mycobacterium fortuitum* NRRL B-8119 in an aqueous nutrient culture medium under aerobic conditions in the presence of a steroid containing from 8 to 10 carbon atoms, inclusive, in the 17-alkyl side chain and isolating said compound in its essentially pure form from the culture medium.

2. A process, according to claim 1, wherein said steroid is sitosterol.

3. A process, according to claim 1, wherein said steroid is cholesterol.

4. A process, according to claim 1, wherein said steroid is stigmasterol.

5. A process, according to claim 1, wherein said steroid is campesterol.

6. A process for preparing 9α-OH testosterone in its essentially pure form which comprises cultivating *Mycobacterium fortuitum* NRRL B-8119 in an aqueous nutrient culture medium under aerobic conditions in the presence of a mixture of two or more steroids wherein each steroid contains from 8 to 10 carbon atoms, inclusive, in the 17-alkyl side chain and isolating said compound in its essentially pure form from the culture medium.

7. A process, according to claim 6, wherein said steroid mixture is selected from the group consisting of sitosterol, cholesterol, stigmasterol, and campesterol.

8. A process for preparing 9α-OH testosterone in its essentially pure form which comprises cultivating a Mycobacterium mutant which is characterized by its ability to selectively degrade steroids having 17-alkyl side chains of from 8 to 10 carbon atoms, inclusive, and accumulate 9α-OH testosterone in the fermentation beer, in an aqueous nutrient culture medium under aerobic conditions in the presence of a steroid containing from 8 to 10 carbon atoms, inclusive, in the 17-alkyl side chain and isolating said compound in its essentially pure form from the culture medium.

9. A process, according to claim 8, wherein said mutant microorganism is cultivated in an aqueous nutrient culture medium under aerobic conditions in the presence of a mixture of two or more steroids wherein each steroid contains from 8 to 10 carbon atoms, inclusive, in the 17-alkyl side chain and isolating said compound in its essentially pure form from the culture medium.

10. A process, according to claim 8, wherein said steroid is selected from the group consisting of sitosterol, cholesterol, stigmasterol, and campesterol.

11. A process, according to claim 9, wherein said steroid mixture is selected from the group consisting of sitosterol, cholesterol, stigmasterol, and campesterol.

* * * * *